(12) United States Patent
Lindstrom et al.

(10) Patent No.: US 7,038,053 B2
(45) Date of Patent: May 2, 2006

(54) PROCESS FOR IMIDAZO[4,5-C]PYRIDIN-4-AMINES

(75) Inventors: Kyle J. Lindstrom, Houlton, WI (US); Luke T. Dressel, Somerset, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/177,948

(22) Filed: Jul. 8, 2005

(65) Prior Publication Data

US 2005/0245516 A1    Nov. 3, 2005

Related U.S. Application Data

(62) Division of application No. 10/856,975, filed on May 28, 2004, now Pat. No. 6,943,255.

(60) Provisional application No. 60/476,338, filed on Jun. 6, 2003.

(51) Int. Cl.
C07D 471/04    (2006.01)
(52) U.S. Cl. .................. 546/117; 544/127
(58) Field of Classification Search .............. 546/117
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Llindstrom et al. |
| 5,482,936 A | 1/1996 | Lindstrom |
| 5,494,916 A | 2/1996 | Lindstrom et al. |
| 5,644,063 A | 7/1997 | Lindstrom et al. |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B1 | 12/2003 | Crooks et al. |
| 6,660,735 B1 | 12/2003 | Crooks et al. |
| 6,660,747 B1 | 12/2003 | Crooks et al. |
| 6,664,260 B1 | 12/2003 | Charles et al. |
| 6,664,264 B1 | 12/2003 | Dellaria et al. |
| 6,664,265 B1 | 12/2003 | Crooks et al. |
| 6,667,312 B1 | 12/2003 | Bonk et al. |
| 6,670,372 B1 | 12/2003 | Charles et al. |
| 6,677,347 B1 | 1/2004 | Crooks et al. |
| 6,677,348 B1 | 1/2004 | Heppner et al. |
| 6,677,349 B1 | 1/2004 | Griesgraber |
| 6,683,088 B1 | 1/2004 | Crooks et al. |
| 6,706,728 B1 | 3/2004 | Hedenstrom et al. |
| 6,743,920 B1 | 6/2004 | Lindstrom et al. |
| 6,756,382 B1 | 6/2004 | Coleman et al. |
| 6,797,718 B1 | 9/2004 | Dellaria et al. |
| 2002/0016332 A1 | 2/2002 | Slade |
| 2002/0055517 A1 | 5/2002 | Smith |
| 2002/0110840 A1 | 8/2002 | Tomai et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0161797 A1 | 8/2003 | Miller et al. |
| 2003/0199538 A1 | 10/2003 | Skwierczynski et al. |
| 2004/0010007 A1 | 1/2004 | Dellaria et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |

(Continued)

FOREIGN PATENT DOCUMENTS

EP    0 394 026    10/1990

(Continued)

OTHER PUBLICATIONS

Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp 511-513, Dec. 12, 1983.

(Continued)

Primary Examiner—Patricia L. Morris
(74) Attorney, Agent, or Firm—Dean A. Ersfeld

(57) ABSTRACT

A process and intermediates for preparing 1H-imidazo[4,5-c]pyridin-4-amines are disclosed. The process includes providing a 7H-imidazo[4,5-c]tetrazolo[1,5-a]pyridine and converting a 7H-imidazo[4,5-c]tetrazolo[1,5-a]pyridine to a 1H-imidazo[4,5-c]pyridin-4-amine.

3 Claims, No Drawings

U.S. PATENT DOCUMENTS

| | | |
|---|---|---|
| 2004/0132766 A1 | 7/2004 | Griesgraber et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |

FOREIGN PATENT DOCUMENTS

| | | |
|---|---|---|
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 02/36592 | 5/2002 |
| WO | WO 02/46194 | 6/2002 |
| WO | WO 03/097641 | 11/2003 |
| WO | WO 04/053057 | 6/2004 |

OTHER PUBLICATIONS

Brennan, et al, "Automated Bioassay of Interferons in Micro-test Plates", *Biotechniques*, Jun./Jul., 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp 1278-1284 (1950).

Jain, et al, "Chemical and Pharmacological Investigations of Some ω-Substituted Alkylamino-3-aminopyridines", *J. Med. Chem.*, pp 87-92 (1968).

Baranov, et al., *Chem. Abs.* 85, 94362, (1976).

Berényi, et al, "Ring Transformation of Condensed Dihydro-as-triazines", *J. Heterocyclic Chem.*, 18, pp 1537-1540 (1981).

Chollet, et al, "Development of a Topically Active Imiquimod Formulation", *Pharmaceutical Development and Technology*, 4(1), pp 35-43 (1999).

Izumi, et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines", *Bioorganic & Medicinal Chemistry*, 11, pp 2541-2550 (2003).

Krenitsky et al., "Imidazo[4,5-c]pyridines (3-Deazapurines) and Their Nucleosides as Immunosuppressive and Antiinflammatory agents", *J. Med. Chem.*, 29, pp. 138-143 (1986).

PROCESS FOR IMIDAZO[4,5-C]PYRIDIN-4-AMINES

CROSS REFERENCE TO RELATED APPLICATIONS

This application is a divisional of U.S. application Ser. No. 10/856,975 filed on May 28, 2004, now U.S. Pat. No. 6,943,255, which claims the benefit of U.S. Provisional Application No. 60/476,338, filed Jun. 6, 2003.

FIELD

This invention relates to processes for preparing 1H-imidazo[4,5-c]pyridin-4-amines and to intermediates for use in preparing 1H-imidazo[4,5-c]pyridin-4-amines.

BACKGROUND

There has been a major effort in recent years to prepare and find compounds that modulate the immune system. Certain 1H-imidazo[4,5-c]pyridin-4-amine compounds useful as immune response modifiers and methods for their preparation are described, for example, in U.S. Pat. Nos. 5,446,153; 5,494,916; 5,644,063; 6,525,064; 6,545,016; and 6,545,017, in International Publication No. WO 02/46194, and in U.S. patent Publication No. 2004/0010007.

However, despite these developments, there is a continuing need for useful, alternative processes and intermediates for preparing immune response modifying 1H-imidazo[4,5-c]pyridin-4-amines.

SUMMARY

It has now been found that 1H-imidazo[4,5-c]pyridin-4-amine compounds of the Formula I

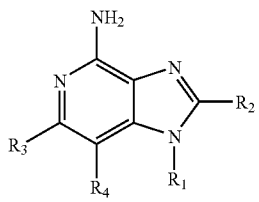

and pharmaceutically acceptable salts thereof, wherein $R_1$ is selected from hydrogen; $CHR_xR_y$ wherein $R_x$ is hydrogen and $R_y$ is selected from alkyl or cyclic alkyl containing one to ten carbon atoms, alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and —C═$CR_zR_z$ wherein each $R_z$ is independently alkyl or cyclic alkyl of one to six carbon atoms;

$R_2$ is selected from hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; benzyl; phenylethyl; phenyl; the benzyl, phenylethyl, or phenyl substituent being optionally substituted on the benzene ring by a moiety selected from methyl, methoxy, and halogen; and morpholinoalkyl wherein the alkyl moiety contains one to four carbon atoms; and $R_3$ and $R_4$ are independently selected from hydrogen and alkyl of one to five carbon atoms, can be prepared by a process comprising the steps of:

providing a compound of Formula VII

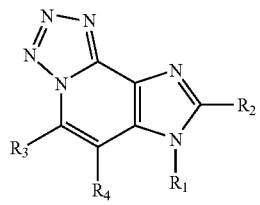

wherein $R_1$, $R_2$, $R_3$, and $R_4$ are as defined above;

reacting the compound of Formula VII with triphenylphosphine to provide an N-triphenylphosphinyl compound of Formula VIII

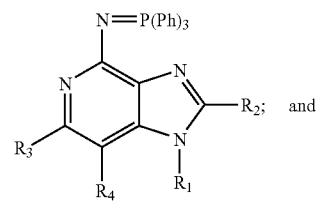

hydrolyzing the N-triphenylphosphinyl compound of Formula VIII to provide a compound of Formula I.

In other embodiments, 1H-imidazo[4,5-c]pyridin-4-amine compounds of the Formula Ia

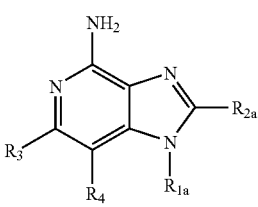

and pharmaceutically acceptable salts thereof, wherein $R_{1a}$ is selected from hydrogen and $CHR_xR_y$ wherein $R_x$ is hydrogen and $R_y$ is selected from alkyl or cyclic alkyl containing one to ten carbon atoms, hydroxyalkyl containing one to six carbon atoms, and alkoxyalkyl wherein the alkoxy moiety contains one to four carbon atoms and the alkyl moiety contains one to six carbon atoms;

$R_{2a}$ is selected from hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; and morpholinoalkyl wherein the alkyl moiety contains one to four carbon atoms; and $R_3$ and $R_4$ are independently selected from hydrogen and alkyl of one to five carbon atoms, can be prepared by a process comprising the steps of:

providing a compound of Formula VIIa

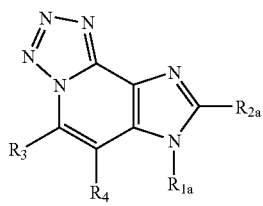

wherein $R_{1a}$, $R_{2a}$, $R_3$, and $R_4$ are as defined above;

reductively removing the tetrazolo ring from the compound of Formula VIIa to provide a compound of the Formula Ia.

In some embodiments the above processes further comprise the step of isolating the compound of Formula I, the compound of Formula Ia, or pharmaceutically acceptable salts thereof.

In another aspect this invention provides intermediate compounds of the Formulas IV–VII, described below, which are useful in the preparation of the compounds of Formula I and Ia, for example, in the processes described herein.

As used herein, the terms "alkyl", "alkenyl", and the prefix "alk-" are inclusive of straight chain and branched chain groups.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

Reaction Scheme I illustrates one embodiment of the invention where $R_1$, $R_2$, $R_3$ and $R_4$ are as defined above.

In step (1) of Reaction Scheme I a 2,4-dichloro-3-nitropyridine of Formula II is reacted with an amine compound of formula $R_1NH_2$, wherein $R_1$ is as defined above, to provide a 2-chloro-3-nitropyridine of Formula III. In some embodiments the compound of formula $R_1NH_2$ is selected from 2-hydroxy-2-methylpropylamine, 2-methylpropylamine, and n-butylamine. The reaction may be carried out in an inert solvent such as N,N-dimethylformamide or dichloromethane in the presence or in the absence of a base such as triethylamine at a reduced temperature, or at an elevated temperature up to the reflux temperature of the solvent. For example, the reaction can be carried out by adding the amine to a solution of a compound of Formula II in a suitable solvent such as N,N-dimethylformamide in the presence of a tertiary amine such as triethylamine at a reduced temperature, e.g., about 0° C. The product can be isolated from the reaction mixture using conventional methods. Many 2,4-dichloro-3-nitropyridines of the Formula II are known and can be readily prepared using known synthetic methods. (See, for example, Dellaria et al, U.S. Pat. No. 6,525,064 and the references cited therein.)

In step (2) of Reaction Scheme I a 2-chloro-3-nitropyridine of Formula III is reacted with an alkali metal azide to provide an 8-nitrotetrazolo[1,5-a]pyridin-7-amine of Formula IV. The reaction can be carried out by combining the compound of Formula III with an alkali metal azide, for example, sodium azide, in a suitable solvent such as N,N-dimethylformamide and heating, for example to about 50–60° C., optionally in the presence of ammonium chloride. Alternatively, the reaction can be carried out by combining the compound of Formula III with an alkali metal azide, for example, sodium azide, in a suitable solvent such as acetonitrile/water, preferably 90/10 acetonitrile/water, in the presence of cerium III chloride, preferably cerium III chloride heptahydrate. Optionally, the reaction can be carried out with heating, for example, at the reflux temperature. The product can be isolated from the reaction mixture using conventional methods.

In step (3) of Reaction Scheme I an 8-nitrotetrazolo[1,5-a]pyridin-7-amine of Formula IV is reduced to provide a tetrazolo[1,5-a]pyridine-7,8-diamine of Formula V. The reduction can be carried out using a conventional heterogeneous hydrogenation catalyst, for example, platinum on carbon or palladium on carbon. The reaction can conveniently be carried out on a Parr apparatus in a-suitable solvent such as ethanol, isopropanol or toluene. Alternatively, $Ni_2B$ can be generated in situ from sodium borohydride and $NiCl_2$ in the presence of methanol. The compound of Formula V is added to the reducing agent solution to effect reduction of the nitro group. When the compound of Formula V contains an alkenylene moiety, the $Ni_2B$ reducing agent can be used without reducing the alkenylene moiety. The product can be isolated from the reaction mixture using conventional methods.

In step (4) of Reaction Scheme I a tetrazolo[1,5-a]pyridine-7,8-diamine of Formula V is reacted with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof, wherein $R_2$ is as defined above and each alkyl contains 1 to 8 carbon atoms, to provide a 7H-imidazo[4,5-c]tetrazolo[1,5-a]pyridine of Formula VII. The reaction can be run in the absence of solvent or in an inert solvent such as, for example, toluene. The reaction may be run in the presence of cyclization conditions, which include sufficient heating (e.g., about 80–150° C.) to drive off any alcohol or water formed as a byproduct of the reaction, and optionally, in the presence of a catalyst such as pyridine hydrochloride. For example, an orthoester of the formula $R_2C(O\text{-alkyl})_3$, (e.g., triethylorthoacetate) is combined with a tetrazolo[1,5-a]pyridine-7,8-diamine of Formula V in toluene in the presence of pyridine hydrochloride and heated at the reflux temperature. The product or a pharmaceutically acceptable salt thereof can be isolated from the reaction mixture using conventional methods.

Alternatively, step 4 can include steps (4a) and (4b) of Reaction Scheme I. In step (4a) a tetrazolo[1,5-a]pyridine-7,8-diamine of Formula V is reacted with a carboxylic acid of the formula $R_2CO_2H$, the corresponding acyl halide, or a mixture thereof, wherein $R_2$ is as defined above, to provide an N-[tetrazolo[1,5-a]pyridin-8-yl]amide of Formula VI. The reaction can be run in an inert solvent such as toluene, dichloromethane, acetonitrile, or pyridine at a reduced temperature, such as about 0° C. For example, an acyl halide can be added to a solution of the compound of Formula V in dichloromethane at about 0° C. in the presence of triethylamine. The product can be isolated from the reaction mixture using conventional methods.

In step (4b) of Reaction Scheme I an N-[tetrazolo[1,5-a]pyridin-8-yl]amide of Formula VI is cyclized to provide a 7H-imidazo[4,5-c]tetrazolo[1,5-a]pyridine of Formula VII. The reaction can be run at an elevated temperature, such as a reflux temperature, sufficient to drive off any water formed as a by-product of the reaction. Optionally, a catalyst such as pyridine hydrochloride can be included. The reaction can be 1H-imidazo[4,5-c]pyridin-4-amine of Formula I. The hydrolysis can be carried out by general methods well known to those skilled in the art, for example, by heating in a lower alkanol in the presence of an acid. The product can be isolated from the reaction mixture using conventional methods as the compound of Formula I or as a pharmaceutically acceptable salt thereof.

Reaction Scheme I

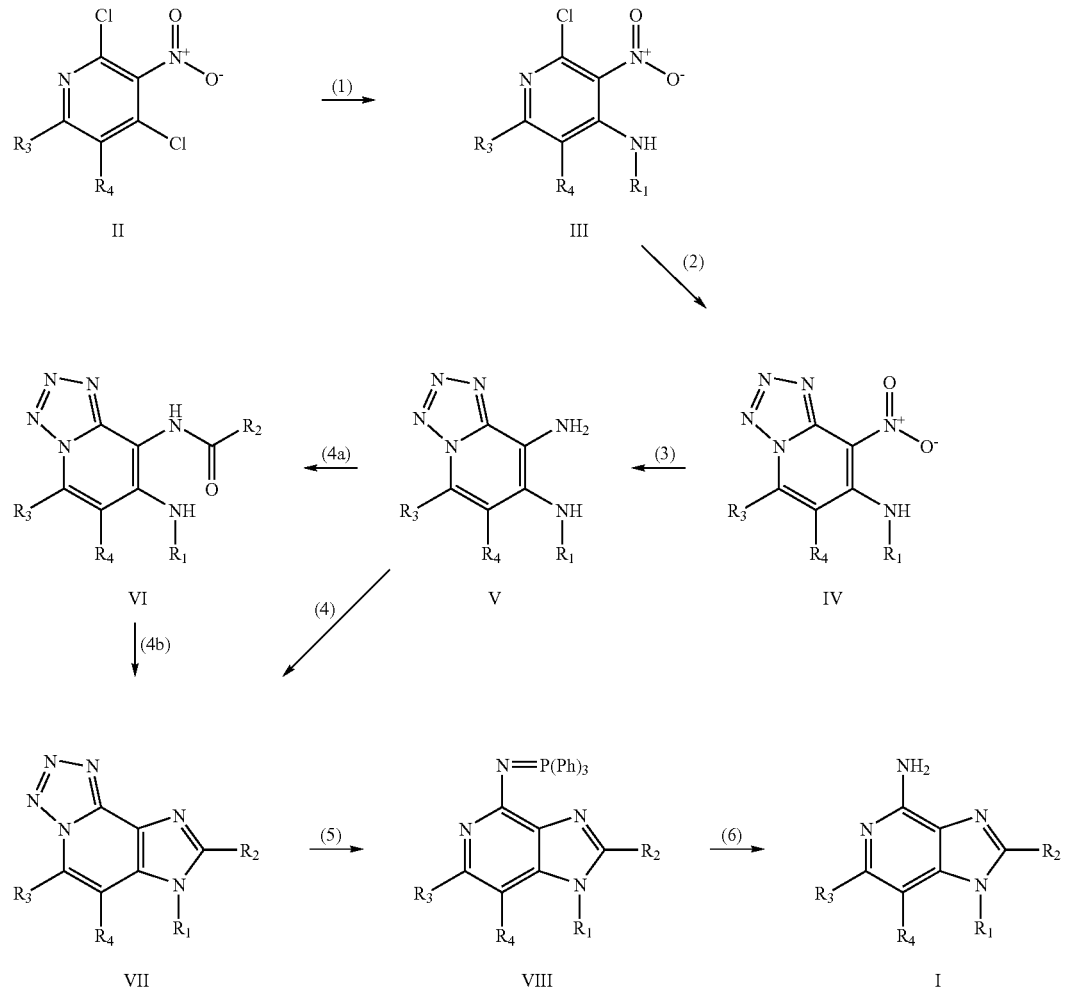

run in the absence of a solvent or in an inert solvent, for example, a solvent have a boiling point of about 80° C. to about 150° C., preferably at least about 100° C., (e.g., toluene, pyridine). The product or a pharmaceutically acceptable salt thereof can be isolated from the reaction mixture using conventional methods.

In step (5) of Reaction Scheme I a 7H-imidazo[4,5-c]tetrazolo[1,5-a]pyridine of Formula VII is reacted with triphenylphosphine to form an N-triphenylphosphinyl intermediate of Formula VIII. The reaction with triphenylphosphine can be run in a suitable solvent such as toluene or 1,2-dichlorobenzene under an atmosphere of nitrogen with heating, for example at the reflux temperature.

In step (6) of Reaction Scheme I an N-triphenylphosphinyl intermediate of Formula VIII is hydrolyzed to provide a Reaction Scheme II also illustrates an embodiment of the invention where $R_{1a}$, $R_{2a}$, $R_3$ and $R_4$ are as defined above.

In step (1) of Reaction Scheme II, the tetrazolo ring is reductively removed from a 7H-imidazo[4,5-c]tetrazolo[1,5-a]pyridine of the Formula VIIa to provide a 1H-imidazo[4,5-c]pyridin-4-amine of the Formula Ia or a pharmaceutically acceptable salt thereof. The reaction can be carried out by reacting the 7H-imidazo[4,5-c]tetrazolo[1,5-a]pyridine of Formula VIIa with hydrogen in the presence of a catalyst and an acid. The reaction can be conveniently run in a Parr apparatus with a suitable catalyst, such as platinum IV oxide, and a suitable acid, such as trifluoroacetic acid or concentrated hydrochloric acid. The product can be isolated from the reaction mixture using conventional methods.

Reaction Scheme II

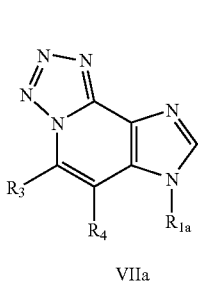

VIIa (1) →

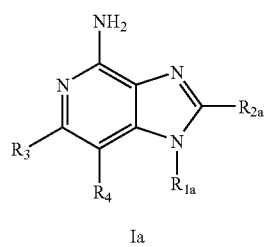

Ia

When an alkenyl, alkenylene, or other readily reducible moiety is present and is to be kept from being reduced during the removal of the tetrazolo ring, steps (5) and (6) of Reaction Scheme I are preferred over Reaction Scheme II. For example, benzyl, phenylethyl, and —C=$R_zR_z$ moieties may be reduced or partially reduced in Reaction Scheme II.

In one embodiment, the present invention provides a process (i) for preparing 1H-imidazo[4,5-c]pyridin-4-amine compounds of the Formula I

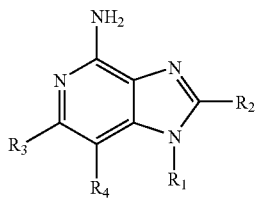

I and pharmaceutically acceptable salts thereof wherein $R_1$, $R_2$, $R_3$, and $R_4$ are as defined above, which process comprises the steps of:

providing a compound of the Formula VII

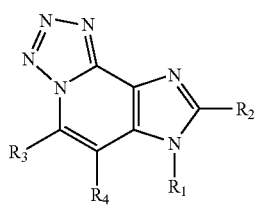

VII wherein $R_1$, $R_2$, $R_3$ and $R_4$ are as defined above;

reacting the compound of Formula VII with triphenylphosphine to provide an N-triphenylphosphinyl intermediate of Formula VIII

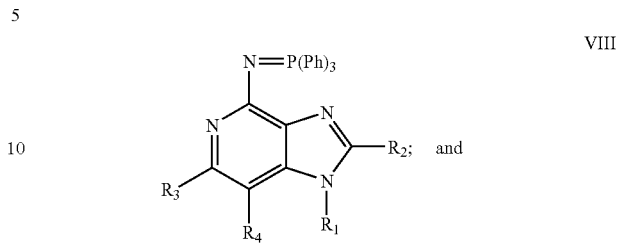

VIII and wherein $R_1$, $R_2$, $R_3$ and $R_4$ are as defined above; and hydrolyzing the N-triphenylphosphinyl intermediate of Formula VIII to provide a compound of Formula I.

In another embodiment, the above process (i) further comprises the step of isolating the compound of Formula I or a pharmaceutically acceptable salt thereof.

In another embodiment, a process (ii) comprises the above process (i) further comprising the steps of:

providing a compound of Formula V

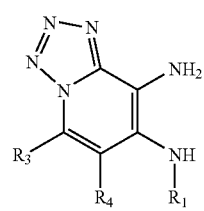

V wherein $R_1$, $R_3$ and $R_4$ are as defined above; and reacting a compound of the Formula V with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof, wherein $R_2$ is as defined above, and each alkyl contains 1 to 8 carbon atoms, to provide a compound of the Formula VII.

In another embodiment, a process (iii) comprises the above process (ii) further comprising the steps of:

providing a compound of Formula IV

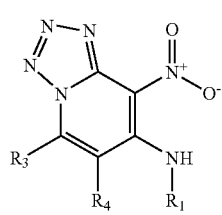

IV wherein $R_1$, $R_3$ and $R_4$ are as defined above; and reducing the compound of Formula IV to provide a compound of the Formula V.

In another embodiment, a process (iv) comprises the above process (iii) further comprising the steps of:
providing a compound of Formula III

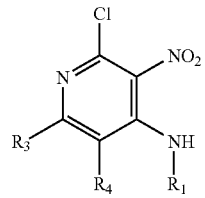

wherein $R_1$, $R_3$ and $R_4$ are as defined above; and reacting the compound of Formula III with an alkali metal azide to provide a compound of the Formula IV. In certain embodiments, the compound of Formula III is reacted with the alkali metal azide in the presence of cerium III chloride.

In another embodiment, a process (v) comprises the above process (iv) further comprising the steps of:
providing a compound of Formula II

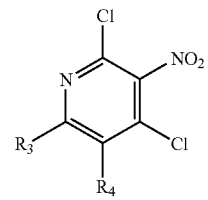

wherein $R_3$ and $R_4$ are as defined above; and reacting the compound of Formula II with a compound of the formula $R_1NH_2$, wherein $R_1$ is as defined above, to provide a compound of the Formula III.

In another embodiment, the above process (v) further comprises the step of isolating the compound of Formula I or a pharmaceutically acceptable salt thereof.

In one embodiment, a process (vi) comprises the above process (i) further comprising the steps of:
providing a compound of Formula VI

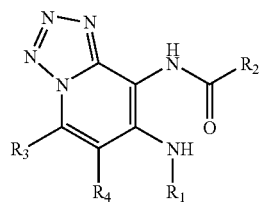

wherein $R_1$, $R_2$, $R_3$ and $R_4$ are as defined above; and subjecting the compound of Formula VI to cyclization conditions, to provide a compound of the Formula VII.

In another embodiment, a process (vii) comprises the above process (vi) further comprising the steps of:
providing a compound of Formula V

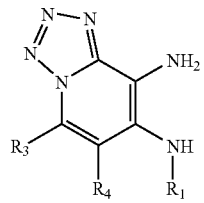

wherein $R_1$, $R_3$ and $R_4$ are as defined above; and reacting a compound of the Formula V with a carboxylic acid of the formula $R_2CO_2H$ or the corresponding acyl halide, wherein $R_2$ is as defined above, to form a compound of the Formula VI.

In another embodiment, a process (viii) comprises the above process (vii) further comprising the steps of:
providing a compound of Formula IV

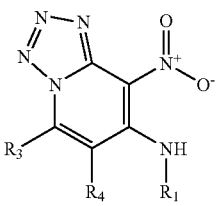

wherein $R_1$, $R_3$ and $R_4$ are as defined above; and reducing the compound of Formula IV to provide a compound of the Formula V.

In another embodiment, a process (ix) comprises the above process (viii) further comprising the steps of:
providing a compound of Formula III

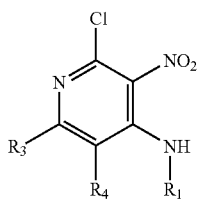

wherein $R_1$, $R_3$ and $R_4$ are as defined above; and reacting the compound of Formula III with an alkali metal azide to provide a compound of the Formula IV. In one embodiment, the compound of Formula III is reacted with the alkali metal azide in the presence of cerium III chloride.

In another embodiment, a process (x) comprises the above process (ix) further comprising the steps of:

providing a compound of Formula II

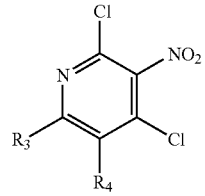

wherein $R_3$ and $R_4$ are as defined above; and reacting the compound of Formula II with a compound of the formula $R_1NH_2$, wherein $R_1$ is as defined above, to provide a compound of the Formula II.

In another embodiment, the process (x) further comprises the step of isolating the compound of Formula I or a pharmaceutically acceptable salt thereof.

In one embodiment, the present invention provides a process (i-a) for preparing 1H-imidazo[4,5-c]pyridin-4-amine compounds of the Formula Ia

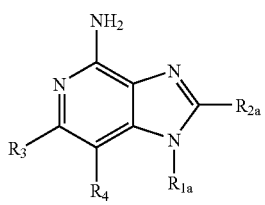

and pharmaceutically acceptable salts thereof, wherein $R_{1a}$, $R_{2a}$, $R_3$, and $R_4$ are as defined above, which process comprises the steps of:

providing a compound of Formula VIIa

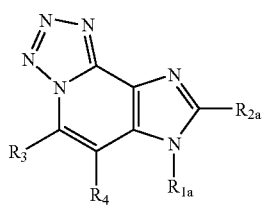

wherein $R_{1a}$, $R_{2a}$, $R_3$, and $R_4$ are as defined above; and reductively removing the tetrazolo ring from the compound of Formula VIIa to provide a compound of the Formula Ia. In one embodiment, the tetrazolo ring is reductively removed by reacting a compound of Formula VIIa with hydrogen in the presence of a catalyst and an acid.

In another embodiment, the above process (i-a) further comprises the step of isolating the compound of Formula Ia or a pharmaceutically acceptable salt thereof.

In another embodiment, a process (ii-a) comprises the above process (i-a) further comprising the steps of:

providing a compound of Formula Va

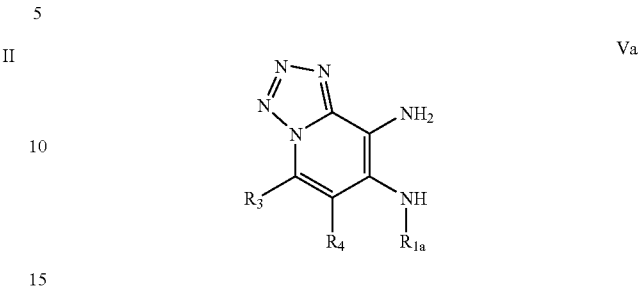

wherein $R_{1a}$, $R_3$ and $R_4$ are as defined above; and reacting a compound of the Formula Va with a carboxylic acid of the formula $R_{2a}CO_2H$; an equivalent thereof selected from the corresponding acyl halide, $R_{2a}C(O\text{-alkyl})_3$, and $R_{2a}C(O\text{-alkyl})_2(O(O=)C\text{-alkyl})$; or a mixture thereof, wherein $R_{2a}$ is as defined above, and each alkyl contains 1 to 8 carbon atoms, to provide a compound of the Formula VIIa.

In another embodiment, a process (iii-a) comprises the above process (ii-a) further comprising the steps of:

providing a compound of Formula IVa

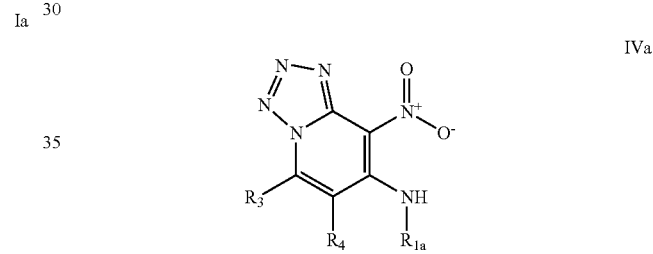

wherein $R_{1a}$, $R_3$ and $R_4$ are as defined above; and reducing the compound of Formula IVa to provide a compound of the Formula Va.

In another embodiment, a process (iv-a) comprises the above process (iii-a) further comprising the steps of:

providing a compound of Formula IIIa

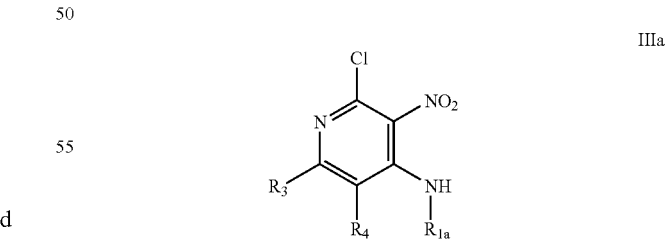

wherein $R_{1a}$, $R_3$ and $R_4$ are as defined above; and reacting the compound of Formula IIIa with an alkali metal azide to provide a compound of the Formula IVa. In another embodiment, the compound of Formula IIIa is reacted with the alkali metal azide in the presence of cerium III chloride.

In another embodiment, a process (v-a) comprises the above process (iv-a) further comprising the steps of:
providing a compound of Formula II

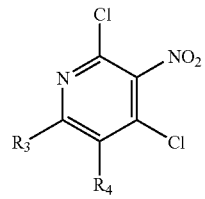

II wherein $R_3$ and $R_4$ are as defined above; and reacting the compound of Formula II with a compound of the formula $R_{1a}NH_2$, wherein $R_{1a}$ is as defined above, to provide a compound of the Formula IIIa.

In another embodiment, the process (iv-a) further comprises the step of isolating the compound of Formula Ia or a pharmaceutically acceptable salt thereof.

In another embodiment, a process (vi-a) comprises the above process (i-a) further comprising the steps of:
providing a compound of Formula VIa

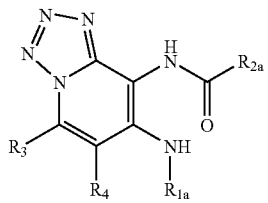

VIa wherein $R_{1a}$, $R_{2a}$, $R_3$ and $R_4$ are as defined above; and subjecting the compound of Formula VIa to cyclization conditions, to provide a compound of the Formula VIIa.

In another embodiment, a process (vii-a) comprises the above process (vi-a) further comprising the steps of:
providing a compound of Formula Va

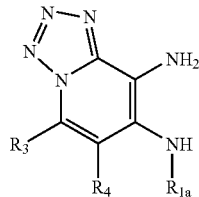

Va wherein $R_{1a}$, $R_3$ and $R_4$ are as defined above; and reacting a compound of the Formula Va with a carboxylic acid of the formula $R_{2a}CO_2H$ or the corresponding acyl halide, wherein $R_{2a}$ is as defined above, to form a compound of the Formula VIa.

In another embodiment, a process (viii-a) comprises the above process (vii-a) further comprising the steps of:
providing a compound of Formula IVa

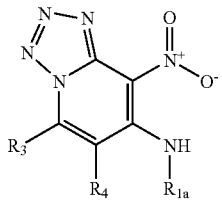

IVa wherein $R_{1a}$, $R_3$ and $R_4$ are as defined above; and reducing the compound of Formula IVa to provide a compound of the Formula Va.

In another embodiment, a process (ix-a) comprises the above process (viii-a) further comprising the steps of:
providing a compound of Formula IIIa

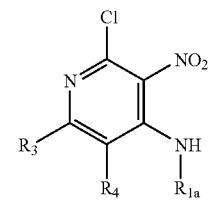

IIIa wherein $R_{1a}$, $R_3$ and $R_4$ are as defined above; and reacting the compound of Formula IIIa with an alkali metal azide to provide a compound of the Formula IVa. In another embodiment the compound of Formula IIIa is reacted with the alkali metal azide in the presence of cerium III chloride.

In another embodiment, a process (x-a) comprises the above process (ix-a) further comprising the steps of:
providing a compound of Formula II

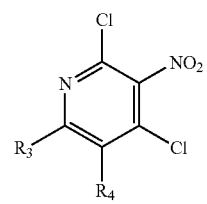

II wherein $R_3$ and $R_4$ are as defined above; and reacting the compound of Formula II with a compound of the formula $R_{1a}NH_2$, wherein $R_{1a}$ is as defined above, to provide a compound of the Formula IIIa.

In another embodiment, the above process (ix-a) further comprises the step of isolating the compound of Formula Ia or a pharmaceutically acceptable salt thereof.

In one embodiment, the present invention provides a process (xi) for preparing a chemical compound comprising the steps of:

providing a compound of Formula III

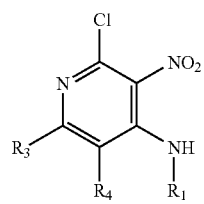

wherein $R_1$, $R_3$ and $R_4$ are defined above; and reacting the compound of Formula III with an alkali metal azide to provide a compound of Formula IV

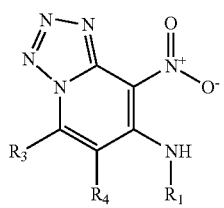

wherein $R_1$, $R_3$, and $R_4$ are as defined above. In another embodiment, the compound of Formula III is reacted with the alkali metal azide in the presence of cerium III chloride.

In another embodiment, the process (xi) further comprises the steps of:

providing a compound of Formula II

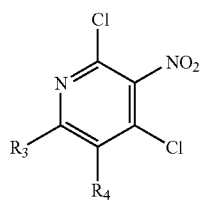

wherein $R_3$ and $R_4$ are as defined above; and reacting the compound of Formula II with a compound of the formula $R_1NH_2$, wherein $R_1$ is as defined above, to provide a compound of Formula III.

In another embodiment, a process (xii) comprises the above process (xi) further comprising the step of reducing the compound of Formula IV to provide a compound of Formula V

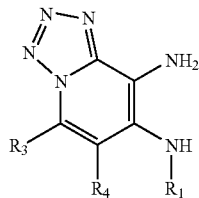

wherein $R_1$, $R_3$, and $R_4$ are as defined above.

In another embodiment, a process (xiii) comprises the above process (xii) further comprising the step of reacting a compound of Formula V with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof, wherein each alkyl contains 1 to 8 carbon atoms; and $R_2$ is as defined above; to provide a compound of the Formula VII

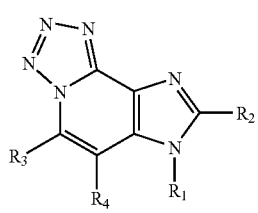

wherein $R_1$, $R_2$, $R_3$, and $R_4$ are as defined above.

In another embodiment, a process (xiv) comprises the above process (xiii) further comprising the step of reacting the compound of Formula VII with triphenylphosphine to provide an N-triphenylphosphinyl intermediate of Formula VIII

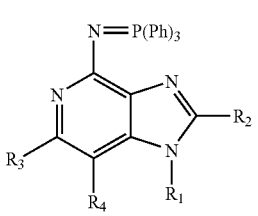

wherein $R_1$, $R_2$, $R_3$, and $R_4$ are as defined above.

In another embodiment, a process (xv) comprises the above process (xii) further comprising the step of (a) reacting the compound of Formula V with a carboxylic acid of the formula $R_2CO_2H$ or the corresponding acyl halide to form a compound of the Formula VI

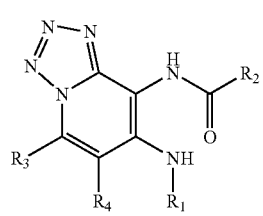

wherein $R_1$, $R_2$, $R_3$, and $R_4$ are as defined above.

In another embodiment, a process (xvi) comprises the above process (xv) further comprising the step of (b) subjecting the compound of Formula VI to cyclization conditions, during step (a) or subsequent to the completion of step (a), to provide a compound of the Formula VII

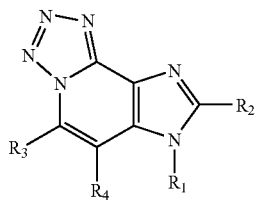

wherein $R_1$, $R_2$, $R_3$, and $R_4$ are as defined above.

In another embodiment, a process (xvii) comprises the above process (xvi) further comprising the step of reacting the compound of Formula VII with triphenylphosphine to provide an N-triphenylphosphinyl intermediate of Formula VIII

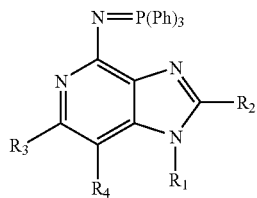

wherein $R_1$, $R_2$, $R_3$, and $R_4$ are as defined above.

In some embodiments, $R_1$, $R_2$, $R_3$, and $R_4$ in the above processes (i), (ii), (iii), (iv), (v), (vi), (vii), (viii), (ix), (x), (xi), (xii), (xiii), (xiv), (xv), (xvi), (xvii), (i-a), (ii-a), (iii-a), (iv-a), (v-a), (vi-a), (vii-a), (viii-a), (ix-a), and (x-a) are independently selected as follows: $R_1$ is selected from alkyl of one to four carbon atoms, alkenyl of two to four carbon atoms, hydroxyalkyl of one to four carbon atoms, alkoxyalkyl wherein the alkoxy moiety contains one to four carbon atoms and the alkyl moiety contains one to four carbon atoms, and phenylethyl; $R_2$ and $R_{2a}$ are selected from alkyl of one to four carbon atoms, hydroxyalkyl of one to four carbon atoms, and alkoxyalkyl wherein the alkoxy moiety contains one to four carbon atoms and the alkyl moiety contains one to four carbon atoms; and $R_3$ and $R_4$ are independently selected from hydrogen and alkyl of one to four carbon atoms. In certain embodiments, $R_1$ is selected from n-butyl, 2-methylpropyl, 2-methyl-1-propenyl, 2-hydroxy-2-methylpropyl, 2-ethoxyethyl, and 2-phenylethyl; $R_2$ and $R_{2a}$ are selected from methyl, ethyl, propyl, butyl, hydroxymethyl, 2-methoxyethyl, and ethoxymethyl; $R_3$ is methyl; and $R_4$ is selected from hydrogen and methyl. In certain embodiments, $R_1$ is selected from 2-hydroxy-2-methylpropyl, 2-methylpropyl, and n-butyl. In certain embodiments, $R_4$ is methyl.

In some embodiments, $R_{1a}$ in the above processes (i-a), (ii-a), (iii-a), (iv-a), (v-a), (vi-a), (vii-a), (viii-a), (ix-a), and (x-a) is independently selected from alkyl of one to four carbon atoms, hydroxyalkyl of one to four carbon atoms, and alkoxyalkyl wherein the alkoxy moiety contains one to four carbon atoms and the alkyl moiety contains one to four carbon atoms. In certain embodiments, $R_{1a}$ is selected from n-butyl, 2-methylpropyl, 2-hydroxy-2-methylpropyl, and 2-ethoxyethyl.

In other embodiments, the above processes (ii), (iii), (iv), (v), (xiii), and (xiv), wherein the compound of Formula V is reacted with a carboxylic acid of the formula $R_2CO_2H$; an equivalent thereof selected from the corresponding acyl halide, $R_2C(O\text{-alkyl})_3$, and $R_2C(O\text{-alkyl})_2(O(O=)C\text{-alkyl})$; or a mixture thereof; and wherein $R_2$ is as defined above, are done in the presence of cyclization conditions to provide a compound of the Formula VII.

In other embodiments, the above processes (ii-a), (iii-a), (iv-a), and (v-a), wherein the compound of Formula Va is reacted with a carboxylic acid of the formula $R_{2a}CO_2H$; an equivalent thereof selected from the corresponding acyl halide, $R_{2a}C(O\text{-alkyl})_3$, and $R_{2a}C(O\text{-alkyl})_2(O(O=)C\text{-alkyl})$; or a mixture thereof; and wherein $R_{2a}$ is as defined above, are done in the presence of cyclization conditions to provide a compound of the Formula VIIa.

In, other embodiments, the alkali metal azide in the above processes (iv), (v), (ix), (x), (iv-a), (v-a), (ix-a), (x-a), (xi), (xii), (xiii), (xiv), (xv), (xvi), (xvii), and (xviii) is sodium azide.

In other embodiments, the compound of Formula IV or IVa is reduced with a heterogeneous hydrogenation catalyst in the above processes (iii), (iv), (v), (viii), (ix), (x), (iii-a), (iv-a), (v-a), (viii-a), (ix-a), (x-a), (xii), (xiii), (xiv), (xv), (xvi), (xvii), and (xviii).

In other embodiments, in the above processes (vii), (viii), (ix), (x), (vii-a), (viii-a), (ix-a), (x-a), (xvi), and (xvii) the compound of Formula V is reacted with the corresponding acyl halide to form the compound of Formula VI, and the compound of Formula VI is subjected to cyclization conditions which include an elevated temperature and the presence of pyridine hydrochloride. In certain embodiments, the acyl halide is ethoxyacetyl chloride.

In some embodiments, in the above processes (i), (ii), (iii), (iv), (v), (vi), (vii), (viii), (ix), (x), (i-a), (ii-a), (iii-a), (iv-a), (v-a), (vi-a), (vii-a), (viii-a), (ix-a), and (x-a) the compound of Formula I or Ia is 2-(ethoxymethyl)-1-(2-methylpropyl)-6-methyl-1H-imidazo[4,5-c]pyridin-4-amine.

In another aspect, the invention provides novel compounds useful as intermediates in the preparation of the compounds of Formulas I and Ia. These intermediates have the structural Formulas IV-VII.

One class of intermediate compounds has the Formula IV:

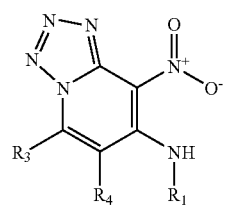

wherein $R_1$ is selected from the group consisting of hydrogen; $CHR_xR_y$, wherein $R_x$ is hydrogen and $R_y$ is selected from the group consisting of alkyl or cyclic alkyl containing one to ten carbon atoms, alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and $—C=CR_zR_z$ wherein each $R_z$ is independently alkyl or cyclic alkyl of one to six carbon atoms; and $R_3$ and $R_4$ are independently selected from the group consisting of hydrogen and alkyl of one to five carbon atoms.

In some embodiments, $R_1$ is selected from alkyl of one to four carbon atoms, alkenyl of two to four carbon atoms, hydroxyalkyl of one to four carbon atoms, alkoxyalkyl wherein the alkoxy moiety contains one to four carbon atoms and the alkyl moiety contains one to four carbon atoms, and phenylethyl; and $R_3$ and $R_4$ are independently selected from hydrogen and alkyl of one to four carbon atoms.

In some embodiments, $R_1$, $R_3$, and $R_4$ are independently selected as follows: $R_1$ is selected from n-butyl, 2-methylpropyl, 2-methyl-1-propenyl, 2-hydroxy-2-methylpropyl, 2-ethoxyethyl, and 2-phenylethyl; $R_3$ is methyl, and $R_4$ is selected from hydrogen and methyl. In some preferred embodiments, $R_3$ and $R_4$ are methyl.

Another class of intermediate compounds has the Formula V

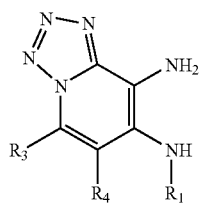

wherein $R_1$, $R_3$ and $R_4$ are selected as described above for intermediate compounds of the Formula IV.

Another class of intermediate compounds has the Formula VI

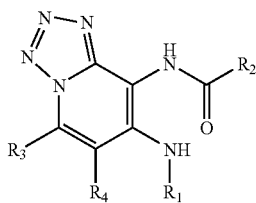

wherein $R_1$, $R_3$ and $R_4$ are selected as described above for intermediate compounds of the Formula IV, and $R_2$ is selected from the group consisting of hydrogen; alkyl containing one to eight carbon atoms, hydroxyalkyl containing one to six carbon atoms; alkoxyalkyl wherein the alkoxy moiety contains one to four carbon atoms and the alkyl moiety contains one to six carbon atoms; benzyl; phenyl ethyl; phenyl; the benzyl, phenylethyl, or phenyl substituent being optionally substituted on the benzene ring by a moiety selected from the group consisting of methyl, methoxy, and halogen; and morpholinoalkyl wherein the alkyl moiety contains one to four carbon atoms.

In some embodiments, $R_2$ is selected from alkyl of one to four carbon atoms, hydroxyalkyl of one to four carbon atoms, and alkoxyalkyl wherein the alkoxy moiety contains one to four carbon atoms and the alkyl moiety contains one to four carbon atoms.

In some embodiments, $R_2$ is selected from methyl, ethyl, propyl, butyl, hydroxymethyl, 2-methoxyethyl, and ethoxymethyl.

Another class of intermediate compounds has the Formula VII

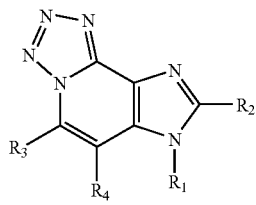

wherein $R_1$, $R_2$, $R_3$, and $R_4$ are selected as described above for the intermediate compound of the Formula VI, and wherein when $R_1$ is hydrogen, at least one of $R_2$, $R_3$, or $R_4$ is other than hydrogen.

The processes of the invention are useful for making compounds and salts of Formulas I and Ia, or for making intermediates which are useful for making such compounds and salts. Compounds and salts of Formulas I and Ia are disclosed in U.S. Pat. No. 5,446,153 as having immunomodulating activity, including, for example, inducing the biosynthesis of interferon, and exhibiting antiviral and antituor activity.

Various aspects and embodiments of the invention are further described by the Examples, which are provided for illustration purposes only and are not intended to be limiting in any way.

EXAMPLES

Example 1

N-(2-Methylpropyl)-5-methyl-8-nitrotetraazolo[1,5-a]pyridin-7-amine

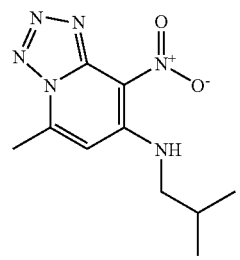

Part A

Under a nitrogen atmosphere, a solution of 2,4-dichloro-6-methyl-3-nitropyridine (125 g, 0.604 mol) in anhydrous N,N-dimethylformamide (625 mL) was cooled to 0° C. Triethylamine (84.2 mL, 0.604 mol) was added. 2-Methylpropylamine (66 mL, 0.664 mol) was added dropwise to the resulting solution over a period of one hour; the reaction reached a temperature of 17° C. and became yellow. The reaction was allowed to warm to room temperature and stir overnight. The reaction mixture was filtered to remove salts, and then the N,N-dimethylformamide was removed under reduced pressure. The crude product was dissolved in ethyl acetate (750 mL), and the solution was washed with water (3×1 L), dried over magnesium sulfate, and then concentrated under reduced pressure. Hexane (300 mL) was added to the resulting yellow oil; the mixture was heated until the oil dissolved and then placed in a freezer. After ten minutes, the recrystallization mixture was seeded with crystals made in a previous run and then left undisturbed for four hours. The resulting precipitate was filtered, washed with cold hexane, and dried in a vacuum oven at room temperature to provide 98 g of 2-chloro-N-(2-methylpropyl)-6-methyl-3-nitropyridin-4-amine.

Part B

Under a nitrogen atmosphere, a mixture of 2-chloro-N-(2-methylpropyl)-6-methyl-3-nitropyridin-4-amine (10.0 g, 41.0 mmol), sodium azide (2.67 g, 41.0 mmol), and anhydrous N,N-dimethylformamide (200 mL) was heated at 60° C. After 5 hours, the dark green solution was allowed to cool to room temperature, poured slowly into water (2 L), and stirred for fifteen minutes. A green precipitate formed, which was filtered and washed with water to yield 9.37 g of N-(2-methylpropyl)-5-methyl-8-nitrotetraazolo[1,5-a]pyridin-7-amine as a light green solid, m.p. 185–187° C.

Example 2

$N^7$-(2-Methylpropyl)-5-methyltetraazolo[1,5-a]pyridine-7,8-diamine

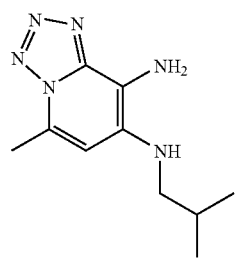

N-(2-Methylpropyl)-5-methyl-8-nitrotetraazolo[1,5-a]pyridin-7-amine (9.60 g, 43.6 mmol) was dissolved in warm anhydrous toluene (900 mL) and methanol (100 mL) and then added to a 2 L stainless steel Parr vessel. The vessel was flushed several times with nitrogen, and 5% platinum on carbon (2.0 g) was added to the solution. The vessel was flushed multiple times with hydrogen, and then placed under hydrogen pressure (50 psi, 3.4×10⁵ Pa). After two hours, no further hydrogen was consumed. The reaction mixture was filtered through a layer of filter agent (available from Aldrich, Milwaukee, Wis. under the trade name CELITE), and the filter cake was washed with hot toluene (1 L). The filtrate was concentrated under reduced pressure to yield 8.5 g $N^7$-(2-methylpropyl)-5-methyltetraazolo[1,5-a]pyridine-7, 8-diamine as a light orange solid, m.p. 159–162° C.

Example 3

2-Ethoxy-N-{7-[(2-methylpropyl)amino]-5-methyltetraazolo[1,5-a]pyridin-8-yl}acetamide

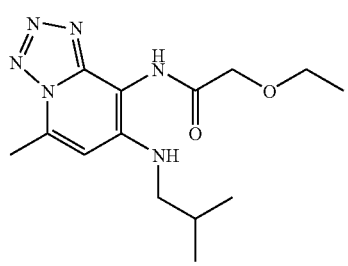

A mixture of $N^7$-(2-methylpropyl)-5-methyltetraazolo[1,5-a]pyridine-7,8-diamine (8.4 g, 38.1 mmol) in anhydrous dichloromethane (300 mL) was cooled to 0° C. under a nitrogen atmosphere, and triethylamine (5.3 mL, 38.1 mmol) was added. A solution of ethoxyacetyl chloride (4.7 g, 38.1 mmol) in dichloromethane (100 mL) was added dropwise over a period of five minutes, and a homogeneous solution resulted. After the solution was stirred for one hour, it was allowed to warm to room temperature, washed with water (2×200 mL), dried over magnesium sulfate, filtered, and concentrated under reduced pressure to provide 11.2 g of 2-ethoxy-N-{7-[(2-methylpropyl)amino]-5-methyltetraazolo[1,5-a]pyridin-8-yl}acetamide as a light tan solid, m.p. 182–185° C.

Example 4

8-(Ethoxymethyl)-7-(2-methylpropyl)-5-methyl-7H-imidazo[4,5-c]tetraazolo[1,5-a]pyridine

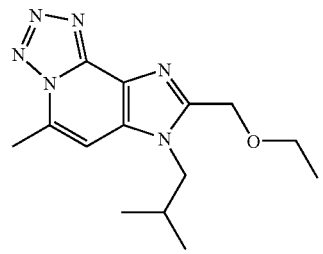

A solution of 2-ethoxy-N-{7-[(2-methylpropyl)amino]-5-methyltetraazolo[1,5-a]pyridin-8-yl}acetamide (10.9 g, 35.6 mmol) and pyridine hydrochloride (10 g) in pyridine (100 mL) was heated at reflux under a nitrogen atmosphere for five days. An analysis by high-performance liquid chromatography indicated the presence of 16% starting material, and an additional 10 g of pyridine hydrochloride was added. After a total of seven days, the reaction was complete, and the solvent was removed under reduced pressure. The resulting black oil was dissolved in ethyl acetate (500 mL), and the solution was washed with water (3×200 mL), dried over magnesium sulfate, filtered, and concentrated to 200 mL. Needles began to form in the solution, which was placed in a freezer for two hours. The crystals were then filtered and washed with cold ethyl acetate to yield 6.85 g of 8-(ethoxymethyl)-7-(2-methylpropyl)-5-methyl-7H-imidazo[4,5-c]tetraazolo[1,5-a]pyridine as light brown needles, m.p. 158–160° C.

Example 5

2-(Ethoxymethyl)-1-(2-methylpropyl)-6-methyl-1H-imidazo[4,5-c]pyridin-4-amine hydrochloride

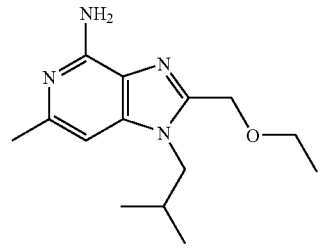

A mixture of 8-(ethoxymethyl)-7-(2-methylpropyl)-5-methyl-7H-imidazo[4,5-c]tetraazolo[1,5-a]pyridine (6.5 g, 22.5 mmol), triphenylphosphine (6.5 g, 24.8 mmol), and toluene (130 mL) was stirred and heated at reflux under nitrogen for 24 hours. Additional triphenylphosphine (3.0 g, 11.4 mmol) was added to the cloudy mixture, and the reaction was continued for three days. The solvent was removed under reduced pressure, and the resulting brown oil was dissolved in methanol (100 mL). Following the addition of a 1.0 M solution of hydrochloric acid in diethyl ether (45 mL) to the methanol solution, the reaction was heated at reflux overnight. The solvents were removed under reduced pressure, and water (200 mL) was added to the resulting brown oil, forming a white precipitate that was removed by filtration. Solid sodium carbonate (6.5 g) was added to the aqueous solution, followed by extraction with dichloromethane (2×200 mL). The combined extracts were dried over magnesium sulfate, filtered, and concentrated under reduced pressure to provide a brown oil, which was dissolved in 2-propanol (45 mL). A 1.0 M solution of hydrochloric acid in diethyl ether (22.5 mL) was added to the solution of crude product, and a white solid formed. After one hour the solid was isolated by filtration, washed with cold 2-propanol and diethyl ether, and dried in a vacuum oven at 90° C. for two days to yield 4.3 g of 2-(ethoxymethyl)-1-(2-methylpropyl)-6-methyl-1H-imidazo[4,5-c]pyridin-4-amine hydrochloride as a white solid, m.p. 181–183° C.

Analysis: Calculated for $C_{14}H_{22}N_4O$ HCl: % C, 56.27; % H, 7.76; % N, 18.75. Found: % C, 56.33; % H, 7.67; % N, 18.90.

Example 6

2-(Ethoxymethyl)-1-(2-methylpropyl)-6-methyl-1H-imidazo[4,5-c]pyridin-4-amine

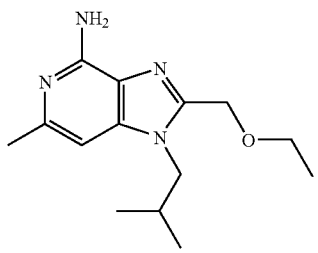

8-(Ethoxymethyl)-7-(2-methylpropyl)-5-methyl-7H-imidazo[4,5-c]tetraazolo[1,5-a]pyridine (6.5 g, 22.5 mmol), trifluoroacetic acid (67 mL), and platinum (IV) oxide (0.47 g) are added to a stainless steel Parr vessel, which is then placed under hydrogen pressure (50 psi, $3.4 \times 10^5$ Pa). For the first eight hours, the vessel is flushed with hydrogen every two hours and then maintained under hydrogen pressure (50 psi, $3.4 \times 10^5$ Pa) overnight. The reaction mixture is filtered through a layer of CELITE filter aid, and the filter cake is washed with additional trifluoroacetic acid. The filtrate is concentrated under reduced pressure to yield a light brown oil, which is dissolved in 37% aqueous hydrochloric acid (25 mL). Sodium carbonate is added to this solution until it exhibits pH 12. The resulting solution is extracted with chloroform. The chloroform solution is dried over magnesium sulfate, filtered, and concentrated under reduced pressure to provide about 4 g of 2-(ethoxymethyl)-1-(2-methylpropyl)-6-methyl-1H-imidazo[4,5-c]pyridin-4-amine as a white solid.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:
1. A compound of the Formula IV

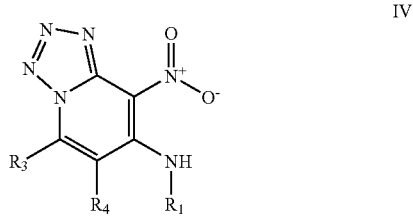

wherein
$R_1$ is selected from the group consisting of hydrogen; $CHR_xR_y$ wherein $R_x$ is hydrogen and $R_y$ is selected from the group consisting of alkyl or cyclic alkyl containing one to ten carbon atoms, alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and —C=$CR_zR_z$ wherein each $R_z$ is independently alkyl or cyclic alkyl of one to six carbon atoms; and $R_3$ and $R_4$ are independently selected from the group consisting of hydrogen and alkyl of one to five carbon atoms.

2. A compound of the Formula V

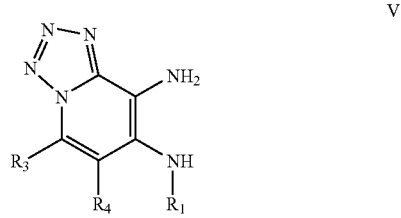

wherein
$R_1$ is selected from the group consisting of hydrogen; $CHR_xR_y$ wherein $R_x$ is hydrogen and $R_y$ is selected from the group consisting of alkyl or cyclic alkyl containing one to ten carbon atoms, alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and —C=$CR_zR_z$ wherein each $R_z$ is independently alkyl or cyclic alkyl of one to six carbon atoms; and $R_3$ and $R_4$ are independently selected from the group consisting of hydrogen and alkyl of one to five carbon atoms.

3. A compound of the Formula VI

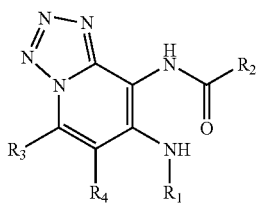

VI wherein $R_1$ is selected from the group consisting of hydrogen; $CHR_xR_y$ wherein $R_x$ is hydrogen and $R_y$ is selected from the group consisting of alkyl or cyclic alkyl containing one to ten carbon atoms, alkenyl containing two to ten carbon atoms, hydroxyalkyl containing one to six carbon atoms, alkoxyalkyl wherein the alkoxy moiety contains one to four carbon atoms and the alkyl moiety contains one to six carbon atoms, benzyl, and phenylethyl; and $-C=CR_zR_z$ wherein each $R_z$ is independently alkyl or cyclic alkyl of one to six carbon atoms;

$R_2$ is selected from the group consisting of hydrogen; alkyl containing one to eight carbon atoms; hydroxyalkyl containing one to six carbon atoms; alkoxyalkyl wherein the alkoxy moiety contains one to four carbon atoms and the alkyl moiety contains one to six carbon atoms; benzyl; phenylethyl; phenyl; the benzyl, phenylethyl, or phenyl substituent being optionally substituted on the benzene ring by a moiety selected from the group consisting of methyl, methoxy, and halogen; and morpholinoalkyl wherein the alkyl moiety contains one to four carbon atoms; and $R_3$ and $R_4$ are independently selected from the group consisting of hydrogen and alkyl of one to five carbon atoms.

* * * * *

UNITED STATES PATENT AND TRADEMARK OFFICE
CERTIFICATE OF CORRECTION

PATENT NO. : 7,038,053 B2
APPLICATION NO. : 11/177948
DATED : May 2, 2006
INVENTOR(S) : Lindstrom, Kyle J.

It is certified that error appears in the above-identified patent and that said Letters Patent is hereby corrected as shown below:

Column 7
Line 29, Delete "H" and insert - - II - -, therefor;

Column 8
Line 16-14,

Delete " 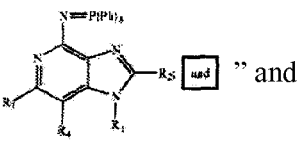 " and

Insert - - 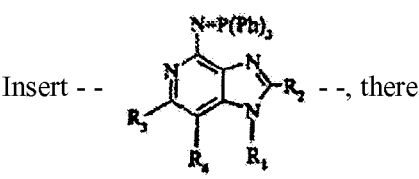 - -, therefore;

Column 11
Line 20, delete "II" and insert - - III - -, therefore;

Column 19
Line 51, After "atoms" delete "," and insert - - ; - -, therefore;

Column 19
Line 55, Delete "phenyl ethyl" and insert - - phenylethyl - -, therefor.

Signed and Sealed this

Twenty-sixth Day of September, 2006

JON W. DUDAS
*Director of the United States Patent and Trademark Office*